United States Patent [19]
Ribier et al.

[11] Patent Number: 5,601,833
[45] Date of Patent: Feb. 11, 1997

[54] PROTECTIVE, NUTRITIVE AND/OR FIRMING COMPOSITION FOR THE SIMULTANEOUS TREATMENT OF THE SURFACE LAYERS AND DEEP LAYERS OF THE SKIN, AND USE THEREOF

[75] Inventors: Alain Ribier; Jean-Thierry Simonnet, both of Paris; Elisabeth Picard, Meudon La Foret; Jacqueline Griat, Ablon, all of France

[73] Assignee: L'Oreal, Paris, France

[21] Appl. No.: 366,741

[22] Filed: Dec. 30, 1994

[30] Foreign Application Priority Data

Dec. 30, 1993 [FR] France .................................. 93 15868

[51] Int. Cl.⁶ .................................................. A61K 9/127
[52] U.S. Cl. ............................................ 424/401; 424/450
[58] Field of Search ................................... 424/401, 450

[56] References Cited

FOREIGN PATENT DOCUMENTS

| 0433131 | 6/1991 | European Pat. Off. . |
| 0559502 | 9/1993 | European Pat. Off. . |
| 2315991 | 1/1977 | France . |
| 2408387 | 6/1979 | France . |
| 2614787 | 11/1988 | France . |

OTHER PUBLICATIONS

Handjani Vila et al., *Chemical Abstracts*, vol. 110, 1989, #29092.
Zabotto et al., *Chemical Abstracts*, vol. 96, 1982, #149189.
Nguyen et al., *Chemical Abstract*, vol. 118, May 1993, #175489.

V. Gabrijelčič et al. "Evaluation of Liposomes as Drug Carriers into the Skin by One–Dimensional EPR Imaging". *International Journal of Pharmaceutics*, vol. 62, pp. 75–79. 1990.

*Primary Examiner*—Thurman K. Page
*Assistant Examiner*—M. Sikha
*Attorney, Agent, or Firm*—Oblon, Spivak, McClelland, Maier & Neustadt, P.C.

[57] ABSTRACT

Compositions comprising a first dispersion of lipid vesicles which are capable of penetrating into the deep layers of the skin and which contain at least one active agent chosen from anti-oxygenated-free-radical agents, proteins, sugars, enzymes, vitamins, nucleotides and sequences thereof, trace elements, coenzymes, unsaturated fatty acid-rich phospholipids, silicon derivatives and plant extracts, for treating these deep layers, and a second dispersion of lipid vesicles which are capable of penetrating into the surface layers of the skin and which contain at least one active agent chosen from screening agents, anti-oxygenated-free-radical agents, sugars, amino acids, vitamins, ceramides, unsaponifiable products derived from plant oils, and components of sweat, for treating these surface layers, are effective protecting, nourishing and/or firming the skin.

17 Claims, No Drawings

PROTECTIVE, NUTRITIVE AND/OR FIRMING COMPOSITION FOR THE SIMULTANEOUS TREATMENT OF THE SURFACE LAYERS AND DEEP LAYERS OF THE SKIN, AND USE THEREOF

BACKGROUND OF THE INVENTION

1. Field of the Invention

The present invention relates to cosmetic and/or dermatological compositions intended to protect, nourish and/or firm the skin, both of the face and of the body, or even of the scalp. It relates more particularly to a composition comprising at least one active agent which is conveyed via at least two distinct types of lipid vesicles. The present invention also relates to a method for protecting, nourishing and/or firming the skin by the topical application of such a composition.

2. Discussion of the Background

The skin is subjected to daily aggression, especially atmospheric aggression, resulting in a drying and/or a depletion of fatty substances in the skin, requiring it to be regularly protected, nourished or even firmed up. Thus, numerous protective, nourishing and/or firming compositions are currently available on the market. Unfortunately, the effectiveness of these compositions is often insufficient, the latter providing only a partial treatment of the skin.

Moreover, many examples are known of cosmetic or dermatological compositions intended for treating the skin, which have one or more active agents that are suitable for treating the skin and which are encapsulated in lipid spherules or vesicles (also known as liposomes).

Lipid spherules or vesicles are understood to refer to particles formed of a membrane consisting of one or more concentric lamellae, these lamellae containing one or more bimolecular layers of amphiphilic lipids encapsulating an aqueous phase. The aqueous phase may contain water-soluble active substances and the bimolecular layers of amphiphilic lipids may contain lipophilic active substances.

These spherules generally have a mean diameter of between 10 nm and 5000 nm. Among the many documents published regarding this matter, there may be mentioned the French Certificate of Addition 2,408,387 which describes a composition based on aqueous dispersions of ionic or nonionic lipid spherules encapsulating at least one active substance. More precisely, this document describes compositions containing at least two dispersions of spherules containing different active agents, for the purpose of obtaining a mixed system, that is to say a system in which a first dispersion of spherules containing a first type of active substance is combined with a second dispersion of spherules containing another type of active substance, which enables the two types of substances to act simultaneously at the time of treatment and possibly to obtain a synergistic effect which would not be produced if these two categories of substances were made to act successively and separately.

It in well known that the skin consists of surface layers, the stratum corneum, and of deep layers, the live epidermis and the dermis. However, specific delivery of such an active agent into the surface layers and, simultaneously, of the same or another active agent into the deep layers, is not known from the prior art.

Thus, there remains a need for a method for protecting, nourishing, and/or firming the skin by simultaneously treating the surface layers and deep layers of the skin. There also remains a need for compositions useful in such methods.

SUMMARY OF THE INVENTION

Accordingly, it is one object of the present invention to provide a novel method for protecting, nourishing, and/or firming the skin.

It is another object of the present invention to provide such a method that simultaneously treats the surface layers and the deep layers of the skin.

It is another object of the present invention to provide novel compositions useful in such methods.

These and other objects, which will become apparent during the following detailed description, have been achieved by the inventors' discovery that compositions comprising:

(a) a first dispersion of lipid vesicles which are capable of penetrating into the deep layers of the skin and which contain at least one active agent chosen from anti-oxygenated-free-radical agents, protides, sugars, enzymes, vitamins, nucleotides and sequences thereof, trace elements, coenzymes, unsaturated fatty acid-rich phospholipids, silicon derivatives and plant extracts, for treating these deep layers; and (b) a second dispersion of lipid vesicles which are capable of penetrating into the surface layers of the skin and which contain at least one active agent chosen from screening agents, anti-oxygenated-free-radical agents, sugars, amino acids, vitamins, ceramides, unsaponifiable products derived from plant oils, and components of sweat, for treating these surface layers, are useful for protecting, nourishing, and/or firming the skin, simultaneously treating the surface layers and the deep layers of the skin.

Protides should also be understood to mean natural amino acids, as well as peptides and proteins.

Thus, the inventors have now developed protective, nutritive and/or firming cosmetic and/or dermatological compositions which allow the simultaneous action of two different active agents, and which furthermore allow these active agents to act in different areas of the skin, that is to say in the surface layers and in the deep layers of the skin, thereby very markedly enhancing the effectiveness of these compositions and the complementary or synergistic effect of the active agents used.

The inventors have also developed protective, nutritive and/or firming cosmetic and/or dermatological compositions which enable the same active agent to act simultaneously in the surface layers and in the deep layers of the skin, providing a more complete and therefore a more effective treatment of the skin.

According to a specific embodiment, the active agents contained in the first dispersion of vesicles and in the second are the same.

DETAILED DESCRIPTION OF THE PREFERRED EMBODIMENTS

The Applicant has used a means of classifying vesicles which enables a person skilled in the art readily to select lipid vesicles capable of conveying the active agent to the deep layers of the skin, known as vesicles with deep-down action, and those capable of conveying the active agent to the surface layers of the skin, known as vesicles acting at the surface.

This classification in made on the basis of the diffusion constant D of a probe introduced into the vesicles. This probe is N-(1-oxyl-2,2,6,6-tetramethyl-4-piperidyl)-N,N- dimethyl-N-hydroxyethylammonium iodide, ASL, of formula (I):

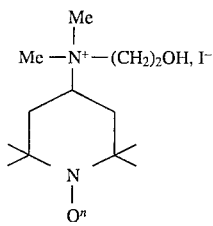

Vesicles for which the diffusion constant D of the probe into the stratum corneum is $<1\times10^{-7}$ cm$^2$ s$^{-1}$ are vesicles which are capable of penetrating into the deep layers of the skin.

Vesicles for which the diffusion constant D of the probe into the stratum corneum is $>1\times10^{-7}$ cm$^2$ s$^{-1}$ are vesicles which are capable of conveying the active agent to the surface layers of the skin.

The vesicles of the first type, the so-called vesicles with deep-down action, are generally in the fluid state at room temperature (about 20° C.), and those of the second type, the so-called vesicles acting at the surface, are generally in the gelled state at room temperature. The means of recognizing the state of the vesicles consists in determining the phase transition temperature (fluid-gel lamellar of the main lipid constituting the membrane thereof) by differential thermal analysis (DTA).

Other characteristics of these vesicles relate to their ability to deliver the active agent to a greater or lesser depth in the skin. This is particularly the case for the degree of encapsulation.

Glucose is a labelling agent conventionally used for this type of determination (see in particular, *Liposomes a practical approach*, by R.R.C. New, IRL Press, pp. 125–136 (1990)).

The degree of encapsulation in expressed as the volume of glucose solution encapsulated in the vesicles, measured in μl relative to the unit weight (mg) of the lipide constituting the membrane. This degree of encapsulation is determined immediately after the step of separation of the free glucose from the encapsulated glucose ($T_0$), as well as twenty-four hours after this separation ($T_{24\ hours}$).

The difference between these two successive determinations illustrates the permeability of the vesicles with respect to the encapsulated glucose, which may also be referred to as their encapsulation potential.

The first type of vesicles (delivering the active agent into the deep layers of the skin) has a high encapsulation potential for the small water-soluble molecules which are conventionally modelled by glucose, this encapsulation potential being maintained for at least 24 hours. The second type of vesicles (delivering the active agent into the surface layers of the skin) does not retain glucose in the encapsulated state for the same amount of time.

The main lipids constituting the vesicles of the first type (deep delivery of the active agent) are composed of at least one linear and saturated fatty chain of length ranging from 16 to 30 carbon atoms, such as hydrogenated phospholipids (from plants or from egg), saturated synthetic phospholipids such as dipalmitoylphosphatidylcholine, and polyol alkyl ethers or polyol alkyl esters containing one, two or three fatty chains per molecule. These lipids are used alone or as a mixture.

The main lipids constituting the vesicles of the second type (active agent delivered at the surface) are chosen in particular from the group comprising ionic lipids, especially such an natural plant- or egg-based phospholipids, containing unsaturated fatty chains having from 16 to 30 carbon atoms; nonionic lipids such as, in particular, polyol alkyl ethers or polyol alkyl esters containing one or more fatty chains per molecule, including at least one fatty chain with a length of less than 16 carbon atoms, such as in lauryl polyglyceryl-6cetearyl glycol ether; and mixtures thereof. The latter compound is described in detail in French Patent Application FR 92-09603 filed by L'Oréal.

It is possible, in a known manner, to incorporate into the lipid phase constituting the lipid membrane of the vesicles at least one additive chosen from the group formed of sterols (phytosterols, cholesterol or polyoxyethylenated phytosterols); long-chain alcohols, diols and triols (phytanetriol), long-chain amines and the quaternary ammonium derivatives thereof; phosphoric esters of fatty alcohols and the alkali metal (Na or K) salts thereof, such as dicetyl phosphate, sodium dicetyl phosphate, alkyl sulfates (sodium cetyl sulfate), alkali metal salts of cholesterol sulfate or of cholesterol phosphate, the sodium salt of phosphatidic acid, and lipoamino acids and the salts thereof, such as the sodium acylglutamates.

Examples of vesicles of the first category (delivering the active agent into the deep layers of the skin) which may be mentioned are vesicles obtained from the following lipids (CTFA name):

A/cholesterol/casein lipoamino acid, especially in a 45/45/10 weight ratio (where A is a triglyceryl cetyl ether marketed by the company Chimex under the name Chimexane NL);

B/cholesterol/dicetyl phosphate, especially in a 60/35/5 weight ratio (where B is a mixture of triglyceryl mono-, di- and tricetyl ether, marketed by the company Chimex under the name Chimexane NT);

Span 40 (from ICI, or sorbitan palmitate)/cholesterol/sodium acylglutamate (sold under the name HS11 by the company Ajinomoto), especially in a 47.5/47.5/5 weight ratio;

PEG 8 stearate/cholesterol/sodium acylglutamate, especially with a 47.5/47.5/5 weight ratio (where PEG 8 stearate is polyethylene glycol containing 8 units of ethylene oxide, marketed by Unichema under the name PEG 400 stearate);

PEG 8 stearate/cholesterol/phytanetriol/sodium acylglutamate, especially with a 47.5/20/27.5/5 weight ratio;

Hydrogenated lecithin/polyoxyethylenated phytosterol containing 5 units of ethylene oxide, especially in a 60/40 weight ratio;

Polyoxyethylenated methylglucose distearate containing 20 units of ethylene oxide/cholesterol/sodium acylglutamate, especially in a 45/45/10 weight ratio (the distearate being, for example, that marketed under the name Glucam E 20 distearate by Amerchol);

A/cholesterol/dicetyl phosphate, especially with a 47.5/47.5/5 weight ratio;

Diglyceryl distearate (for example that marketed by Nihon under the name Emalex DS G2)/cholesterol/sodium acylglutamate, in a 45/45/10 weight ratio;

Sucrose mono- and distearate (for example Grilloten PSE 141 G from Grillo)/cholesterol/sodium acylglutamate, especially in a 45/45/10 weight ratio;

Tetraglyceryl tristearate (for example Tetraglyn 3S from Nikkol)/cholesterol/sodium acylglutamate, especially in a 45/45/10 weight ratio.

Examples of vesicles of the second type (delivering the active agent into the surface layers of the skin) which may be mentioned are vesicles obtained from the following lipids:

Sunflower lecithin;

Natipide II (soya lecithin/ethanol/water in a 20/16/64 weight ratio, marketed by Nattermann);

C (soya lecithin/cholesterol/propylene glycol in a 60/20/20 weight ratio, marketed by Nattermann under the name NAT 50 PG);

D/dimyristyl phosphate, especially in a 95/5 weight ratio (where D is a lauryl polyglyceryl-6-cetearyl glycol ether marketed by Chimex under the name Chimexane NS).

Table I below gives, for some of the vesicles obtained using the above lipids, the diffusion constant D of ASL in the stratum corneum and in the epidermis/dermis, as well as the degree of encapsulation of glucose and the phase transition temperature of the main lipid constituting the membrane. The diffusion constant was measured for an encapsulated ASL concentration of 0.35% by weight based on the total weight of the composition.

nitroxide reduction kinetic imaging" by V. Gabrijelcic et al., *Periodicum Biogorum*, vol. 93, No. 2, pp. 245–246 (1991).

Measurement of the degree of encapsulation is carried out as described in the *Liposomes a practical approach*, by R.R.C. New, IRL Press, pp. 125–136 (1990) cited above, and that of the phase transition temperature is carried out as described above.

The active agents with deep-down action and the agents acting at the surface are those which are conventionally used in the cosmetic or dermatological field.

The protective agents delivered at the surface are particularly UV-A and/or UV-B screening agents, pigments or nanopigments.

Screening agents which may be mentioned as a guide are: p-aminobenzoic acid and derivatives thereof (glyceryl, ethyl and isobutyl esters); anthranilates (such as o-aminobenzoate or the alkyl esters thereof); salicylates (amyl, phenyl, benzyl and dipropylene glycol esters); cinnamic acid derivatives (amyl and benzyl esters); dihydroxycinnamic acid derivatives (umbelliferone); trihydroxycinnamic acid derivatives (esculetin); hydrocarbons (stilbene); dibenzalacetone and benzalacetophenone; coumarin derivatives; hydroxy- or

TABLE I

| Ref. | LIPID SYSTEMS | Proportions % by weight (mg) | Diffusion coefficient D in $10^{-7}$ cm$^2$ s$^{-1}$ | | Degree of encapsulation of glucose in μl/mg | | Phase transition temperature in °C. |
|---|---|---|---|---|---|---|---|
| | | | in the stratum corneum | in the epidermis/ dermis | $T_o$ | $T_{24h}$ | |
| | 1st type - deep down | | | | | | |
| 1 | A/cholesterol/casein lipoamino acid | 45/45/10 (67.5/67.5/15) | 42 | 5 | 7.5 | 6.8 | 50 |
| 2 | B/cholesterol/dicetyl phosphate | 60/35/5 (90/52.5/7.5) | 58 | 2 | 11.1 | 11.1 | 54 |
| 3 | Span 40/cholesterol/ sodium acylglutamate | 47.5/47.5/5 (71.25/71.25/7.5) | 42 | 2 | 13.8 | 13.8 | 50 |
| 4 | PEG 8 stearate/ cholesterol/sodium acylglutamate | 47.5/47.5/5 (71.25/71.25/7.5) | 42 | 2 | 14.4 | 14.4 | 55 |
| 5 | PEG 8 stearate/ cholesterol/phytanetriol/ sodium acylglutamate | 47.5/20/27.5/5 71.25/30/ 41.25/7.5) | 8.3 | 2.5 | 4.1 | 3.0 | 55 |
| 6 | Hydrogenated lecithin/ polyoxyethylenated phytosterol | 60/40 (90/60) | 8 | 2 | 6.0 | 4.8 | 80 |
| | 2nd type - surface | | | | | | |
| 7 | Sunflower lecithin | 100 (150) | 0.3 | 0.2 | 1.6 | 0 | <0 |
| 8 | Natipide II (soya lecithin/ethanol/water) | 20/16/64 (30/24/96) | 0.4 | 0.2 | 0.4 | 0 | <0 |
| 9 | C (soya lecithin/ sterols/propylene glycol) | 60/20/20 (90/30/30) | 0.25 | 0.1 | 1.8 | 0 | <0 |
| 10 | D/dimyristyl phosphate | 95/5 (142.5/7.5) | 0.3 | 0.2 | 2.0 | 0 | 14 |

Measurement of the diffusion constant D is carried out by combining two methods using a paramagnetic probe, ASL: one-dimensional and periodic electron paramagnetic resonance (EPR), on the one hand, and EPR kinetic imaging, on the other hand. These two methods are respectively described in the articles "Evaluation of liposomes as drug carriers into the skin by one-dimensional EPR imaging" by V. Gabrijelcic et al., *International Journal of Pharmaceutics*, vol. 62, pp. 75–79, Elsevier (1990), and "Liposome endrapped molecules penetration into the skin measured by methoxy-substituted benzophenones; tannic acid and derivatives thereof; benzophenones and any other sunscreen agent conventionally used in the cosmetic and/or dermatological field, such as benzylidenecamphor, benzene-1,4di-(3-methylidene-10-camphorsulfonic) acid or alternatively 4-(3-methylidenecamphor)phenyltrimethylammonium methyl sulfate, 2-ethylhexyl 2-cyano-3,3'-diphenylacrylate or alternatively dibenzoylmethane, as well as mixtures thereof.

Pigments or nanopigments which may be mentioned are zinc oxide and/or titanium oxide ($TiO_2$, $ZnO_2$).

As anti-oxygenated-free-radical agents acting at the surface which may be used in the present invention, there may be mentioned vitamin E, caffeine, mannitol, extracts of balm, and certain enzymes such as superoxide dismutases, glutathione peroxidase and catalases. Like the screening agents, these active agents are more intended for protecting the skin.

Other active agents acting at the surface for protecting the skin which may also be used are vitamin E and derivatives thereof, γ-orizanol, and salicylic acid and the derivatives thereof, such as 5-n-octanoylsalicylic acid.

The agents acting at the surface for nutrition of the skin are particularly amino acids (glycine, alanine, threonine and citrulline), components of sweat (lactic acid, sodium chloride, urea and serine); sugars (mannose, fructose, galactose and N-acetylglucosamine); and unsaponifiable products derived from natural oils such as jojoba oil, olive oil or soya oil; natural or synthetic ceramides (oleoyldihydrosphingosine).

As anti-oxygenated-free-radical agents which may be used as agents with deep-down action, there may be mentioned nitroxide radicals, for example those cited in the document from L. B. Volodarsky "Advances in the chemistry of stable nitroxides, *Jansen Chimica Acta*, vol. 8, No. 3, pp. 12–19 (1990) and more especially the radicals 2,2,6, 6-tetramethylpiperidine 1-oxide, 4-hydroxytetramethylpiperidine 1-oxide, N-tert-butyl-alpha-phenylnitrone, docylcyclohexane, N-(1-oxyl-2,2,6,6-tetramethyl-4-piperidyl)-N,N-dimethyl-N-hydroxyethylammonium salts, such as N-(1-oxyl-2,2,6,6-tetramethyl-4-piperidyl)-N,N-dimethyl-N-hydroxyethylammonium iodide, ASL, and mixtures thereof. Glycerine, guanosine, anti-elastases, and enzymes such an superoxide dimutases, peroxydases and catalases, may also be used. These anti-free-radical agents are more intended for protecting the skin.

Protides are active agents with deep-down action which are more especially intended for the nutrition, or even the firming, of the skin. These protides are in particular proteins such as milk proteins, yeast proteins or collagens; peptides, especially from corn, from soya and from almond.

The soya protein dispersions (sold by the Laboratoires S ériobiologiques, Nancy, under the name Elesergyl) and the peptides from seeds, especially from soya, are more intended for deep-down firming.

The sugars intended for the deep-down treatment of the skin for the purpose of nourishing it are particularly those mentioned above.

The enzymes which may be used for the deep-down nutrition of the skin are particularly lipases, proteases, glycosidases, and DNA-repair enzymes.

The vitamins which may be used for the deep-down nutrition of the skin are especially vitamins $B_2$ H, C, E, F, and A and derivatives thereof, such as the esters thereof, which are conventionally used by those skilled in the art (magnesium ascorbyl phosphate, retinol acetate or palmitate, tocopherol acetate, etc.) and D-panthenol.

The nucleotides and the sequences thereof which may be used in the invention are more especially intended for the deep-down nutrition of the skin and are especially adenosine di- or triphosphate and deoxyribonucleic acid.

The trace elements are especially intended for the deep-down nutrition of the skin and are, for example, Cu, Zn, Se, Fe and Mg.

The coenzymes, such as NADH (nicotinamide adenine dinucleotide hydrogenase) or NADPH (nicotinamide adenine dinucleotide phosphate hydrogenase), are more intended for the deep-down nutrition, or even firming, of the skin.

The unsaturated fatty acid-rich phospholipids which may be used in the invention for the deep-down treatment are particularly animal oils and especially oils from fish (cod, etc.) or from plants (wheat germ, blackcurrant seed or rosa mosqueta).

As plant extracts which may be used in the invention as agents with deep-down action, there may be mentioned cytoplasmic juices from plants and especially from seaweed or from plant cells cultured in a fermenter.

The silicon derivatives, such as methylsilanol mannuronate (sold under the name Alginium by Exsymol), are intended for deep-down firming.

An other active agents with deep-down action for firming which may be used in the present invention, there may be mentioned anti-elastase active agents such as fatty acids coupled with sugar derivatives or with protein derivatives, such as stearic acid coupled with chondroitin sulfate (sold by Coletica under the name Lifidrem CMST) or such as the mixture of dipalmitoylhydroxyproline and palmitic acid in a 75/25 ratio (sold by Seppic under the name Lipacide BPHP).

Depending on whether the active agents are hydrophilic or lipophilic, they will combine either with the aqueous phase encapsulated in the lipid lamellae or with the lipids constituting these lamellae.

The agents active at the surface and the agents with deep-down action may be present in an amount of from 0.05 to 10% by weight, preferably 0.1 to 5% by weight, based on the total weight of the composition. In addition, the two types of vesicles may contain other types of cosmetic active agents, such as moisturizing agents, keratolytic agents and depigmenting agents or essential oils.

Advantageously, several active agents are used simultaneously in each type of vesicles, these active agents having the same function and/or imparting to the skin, at the surface and deep down, the same type of effect (nutritive, protective or firming); the agents active at the surface and the agents with deep-down action are thus complementary.

The compositions according to the invention may be provided in all the pharmaceutical forms normally used for topical application, such an aqueous gels, emulsions, lotions, ointments, sera and, more particularly, vesicle-dispersed oil droplets such as those described in French patents FR-A-2,485,921 and FR-A-2,490,504.

As is known, in addition to the vesicles, a vegetable oil, mineral oil, silicone-containing oil or synthetic oil which is dispersed in an aqueous phase, and also hydrophilic adjuvants such as gelling agents, preserving agents, opacifying agents, lipophilic adjuvants such as essential oils and fragrances, pigments and fillers, may be found in the compositions of the invention, as described in the above French patents. The dispersed oil may be present in an amount of from 2 to 40% by weight, preferably 5 to 20% by weight, based on the total weight of the composition, and the adjuvants may be present in a total amount of from 0.1 to 10% by weight, preferably 1 to 5% by weight, based on the total weight of the composition.

The invention also relates to a use of the composition defined above for protecting, nourishing and/or firming the skin of the face and/or of the body.

Another aspect of the invention is a cosmetic treatment process for protecting, nourishing and/or firming the skin, by applying the composition defined above to the skin.

The vesicles of both the first and second types suitably comprise 1 to 90% by weight, preferably 5 to 70% by weight, more preferably 5 to 20% by weight, of the total weight of the composition.

The relative amounts of the vesicles of the first and second types in the present compositions are suitably:

10 to 90% by weight of the vesicles of the first type, and 90 to 10% by weight of the vesicles of the second type, preferably:

30 to 70% by weight of the vesicles of the first type, and 70 to 30% by weight of the vesicles of the second type, based on the total weight of the vesicles of the first and second types.

Other features of the invention will become apparent in the course of the following descriptions of exemplary embodiments which are given for illustration of the invention and are not intended to be limiting thereof.

EXAMPLES

In the Examples below, the term "qs 100 g" means that ingredient is added in an amount sufficient to make the sum of the amounts of all ingredients equal 100 g.

A. Production of lipid vesicles containing ASL.

The constituent lipids of the wall of the vesicles are weighed and dissolved in 10 ml of methanol. The alcoholic solution is then transferred into a 50 ml round-bottomed flask with a ground joint, which is subsequently placed on a rotary evaporator such that the contents are thermostatted at a temperature of 30° C. The evaporation is continued until a dry film of lipids is deposited on the wall of the flask.

3 ml of an aqueous 0.01 molar solution of ASL are then added to the flask, which is subsequently shaken by hand for about 10 minutes, either at room temperature (20° C.) for the vesicles of Table I of reference Nos. 7 to 10, or at a temperature of 50° C. for the vesicles of reference Nos. 1 to 6 of Table I. The medium is then left to equilibrate at room temperature for 2 hours, after which the dispersion is placed in a dialysis bag and in contact with 500 ml of distilled water. Dialysis takes place overnight. The next day, the water is changed, and the dialysis is continued for a further 4 hours.

A cotton thread 0.3 mm thick is then soaked in the vesicle dispersion and then placed in contact with a section of skin cut from a pig's ear which has been freshly taken from an abattoir intended for food supply.

The ear sample taken is rinsed with water and cut into slices 1 mm thick, 5 mm wide and 10 mm long and then placed in a maintenance cell. Measurements of the diffusion of ASL into the skin are made in the 24 hours following the taking of the skin sample.

B. Production of the cosmetic composition.

1. Production of vesicles of the first type (diffusing deep down).

The vesicles (with deep-down action) are prepared according to a common method for co-fusion of the membrane constituents chosen (see Table I). Thus, the membrane constituent having the lowest melting point $T_m$ is melted; the other membrane constituents are added thereto, and the mixture is then homogenized with moderate stirring and is finally partially hydrated, while maintaining the melting temperature $T_m$ defined above.

An aqueous solution of at least one first active agent for the deep-down treatment is added to the paste obtained. The mixture is stirred with a turbine for 1 hour and 30 minutes in order to hydrate fully, while maintaining the temperature $T_m$. One or more other active agents for the deep-down treatment are added to the reaction medium, homogenization is carried out, and the temperature of the medium is lowered to room temperature (20° C.).

2. Production of vesicles of the second type (diffusing at the surface).

An aqueous solution of one (or more) second active agent for the surface treatment is introduced, at room temperature (20° C.) and with simple stirring, into the chosen mixture of constituents which are to form the membrane of the vesicles acting at the surface (see Table I). Vesicles acting at the surface encapsulating the second active agent acting at the surface are thus obtained.

3. Production of the "double-liposome" composition.

The fatty phase (the oils) of the composition is added to the medium containing the vesicles with deep-down action, and it is dispersed (at room temperature) with stirring. The reaction medium obtained is then mixed with that containing the vesicles acting at the surface. The adjuvants, such as preserving agents, a gelling agent which may be neutralized if necessary with a base (triethanolamine or sodium hydroxide), and fragrances, etc., are then optionally added.

The product obtained is in the form of a soft and smooth white cream which may be used in the cosmetic and/or dermatological field for protecting, nourishing and/or firming the skin at the surface and deep down. This cream may be used daily.

A specific example of a cosmetic composition in accordance with the invention is given below.

Example 1: Nutritive and protective double-liposome cream.

| Liposomes with deep-down action: | |
| --- | --- |
| PEG 8 stearate | 1.4 g |
| Cholesterol | 1.4 g |
| Sodium acylglutamate | 0.2 g |
| Alpha-tocopherol (active agent) | 0.15 g |
| Riboflavin (active agent) | 0.005 g |
| Biotin (active agent) | 0.02 g |
| Panthenol (active agent) | 1.5 g |
| Citric acid (active agent) | 0.02 g |
| Liposomes active at the surface: | |
| Chimexane NS | 0.95 g |
| Dimyristyl phosphate | 0.05 g |
| Methyl octyl cinnamate (active agent) | 0.1 g |
| Oleoyldihydrosphingosine (active agent) | 0.05 g |
| Glycerine | 3.0 g |
| Fatty phase: | |
| Rosa mosqueta oil | 1.0 g |
| Rice oil | 1.0 g |
| Apricot almond oil | 15 g |
| Soya oil | 7 g |
| Fragrance | 0.3 g |
| Aqueous phase: | |
| Carboxyvinyl polymer (gelling agent) | 0.5 g |
| Sodium hydroxide | 0.2 g |
| Preserving agents | 0.2 g |
| Demineralized water | qs 100 g |

This application is based on French Patent Application 93-15868 filed on Dec. 30, 1993, which is incorporated herein by reference in its entirety.

Obviously, numerous modifications and variations of the present invention are possible in light of the above teachings. It is therefore to be understood that, within the scope of the appended claims, the invention may be practiced otherwise than as specifically described herein.

What is claimed as new and is desired to be secured by Letters Patent of the United States is:

1. A protective, nourishing and/or firming composition for the simultaneous treatment of the layers of the stratum corneum and deep layers of the skin, comprising a dispersion mixture of:

(a) a first dispersion of lipid vesicles which are capable of penetrating into the deep layers of the skin and which contain at least one active agent selected from the group consisting of protective, nutritive and firming agents, for treating these deep layers and (b) a second dispersion of lipid vesicles which are capable of penetrating into the layers of the stratum corneum of the skin and which contain at least one active agent selected from the group consisting of protective and nutritive agents, for treating these layers of the stratum corneum, and wherein said vesicles of said first dispersion ensure a distribution of N-(1oxyl-2,2,6,6-tetramethyl-4-piperidyl)-N-dimethyl-N-hydroxyethylammonium iodide (ASL) in the stratum corneum $>1 \times 10^{-7}$ cm$^2$/s and in that said vesicles of said second dispersion ensure a distribution of ASL in the stratum corneum $<1 \times 10^{-7}$ cm$^2$/s.

2. A nourishing composition for the simultaneous treatment of the layers of the stratum corneum and deep layers of the skin, comprising a dispersion mixture of:

(a) a first dispersion of lipid vesicles which are capable of penetrating into the deep layers of the skin and which contain at least one active agent selected from the group consisting of nutritive and firming agents, for treating these deep layers; and (b) a second dispersion of lipid vesicles which are capable of penetrating into the layers of the stratum corneum of the skin and which contain at least one active agent selected from the group consisting of protective and nutritive agents, for treating these layers of the stratum corneum, and wherein said vesicles of said first dispersion ensure a distribution of N-(1-oxyl-2,2,6,6-tetramethyl-4-piperidyl)-N-dimethyl-N-hydroxyethylammonium iodide (ASL) in the stratum corneum $>1 \times 10^{-7}$ cm$^2$/s and in that said vesicles of said second dispersion ensure a distribution of ASL in the stratum corneum $<1 \times 10^{-7}$ cm$^2$/s.

3. A protective composition for the simultaneous treatment of the layers of the stratum corneum and deep layers of the skin, comprising a dispersion mixture of:

(a) a first dispersion of lipid vesicles which are capable of penetrating into the deep layers of the skin and which contain at least one active agent which is an anti-oxygenated-free-radical agent, for treating these deep layers and (b) a second dispersion of lipid vesicles which are capable of penetrating into the layers of the stratum corneum of the skin and which contain at least one active agent selected from the group consisting of screening agents and anti-oxygenated-free-radical agents, for treating these layers of the stratum corneum, and wherein said vesicles of said first dispersion ensure a distribution of N-(1-oxyl-2,2,6,6-tetramethyl-4-piperidyl)-N-dimethyl-N-hydroxyethylammonium iodide.(ASL) in the stratum corneum $>1 \times 10^{-7}$ cm$^2$/s and in that said vesicles of said second dispersion ensure a distribution of ASL in the stratum corneum $<1 \times 10^{-7}$ cm$^2$/s.

4. A method of protecting the skin, comprising applying to the skin of a subject in need thereof an effective amount of a composition comprising a dispersion mixture of:

(a) a first dispersion of lipid vesicles which are capable of penetrating into the deep layers of the skin and which contain at least one active agent which is an anti-oxegenated-free-radical agent, for treating these deep layers and (b) a second dispersion of lipid vesicles which are capable of penetrating into the layers of the stratum corneum of the skin and which contain at least one active agent selected from the group consisting of screening agents and anti-oxygenated-free-radical agents, for treating these layers of the stratum corneum, and wherein said vesicles of said first dispersion ensure a distribution of N-(1-oxyl-2,2,6,6-tetramethyl-4-piperidyl)-N-dimethyl-N-hydroxyethylammonium iodide (ASL) in the stratum corneum $>1 \times 10^{-7}$ cm$^2$ /s and in that said vesicles of said second dispersion ensure a distribution of ASL in the stratum corneum $<1 \times 10^{-7}$ cm$^2$/s.

5. The composition of claim 1, wherein said vesicles of said first dispersion are in a fluid state at room temperature and said vesicles of said second dispersion are in a gelled state at room temperature.

6. The composition of claim 1, wherein said vesicles of said first dispersion exhibit an encapsulation potential of glucose for at least 24 hours, and said vesicles of said second dispersion exhibit an encapsulation potential of glucose for less than 24 hours.

7. The composition of claim 1, wherein said vesicles of said first dispersion are formed of lipids having of at least one linear and saturated fatty chain having from 16 to 30 carbon atoms.

8. The composition of claim 1, wherein said vesicles of said first dispersion are formed of at least one lipid selected from the group consisting of natural hydrogenated phospholipids, saturated synthetic phospholipids, polyol alkyl ethers containing at least one linear fatty chain, polyol alkyl esters containing at least one fatty chain, and mixtures thereof.

9. The composition of claim 1, wherein said vesicles of said first dispersion are formed of at least one lipid selected from the group consisting of:

triglyceryl cetyl ether/cholesterol/casein lipoamino acid; mixtures of triglyceryl mono-, di- and tricetyl ether/cholesterol/dicetyl phosphate; triglyceryl cetyl ether/cholesterol/dicetyl phosphate; sorbitan palmitate/cholesterol/sodium acylglutamate; PEG 8 stearate/cholesterol/sodium acylglutamate; diglyceryl distearate/cholesterol/sodium acylglutamate; sucrose mono- and distearate/cholesterol/sodium acylglutamate; PEG 8 stearate/cholesterol/phytanetriol/sodium acylglutamate; polyoxyethylenated methylglucose distearate containing 20 mol of ethylene oxide/cholesterol/sodium acylglutamate; hydrogenated lecithin/polyoxyethylenated phytosterol; and tetraglyceryl tristearate/cholesterol/sodium acylglutamate.

10. The composition of claim 1, wherein said vesicles of said second dispersion are formed of lipids selected from the group consisting of natural ionic phospholipids having unsaturated fatty chains having from 16 to 30 carbon atoms, polyol alkyl ethers or polyol alkyl esters having one or more fatty chains per molecule, including at least one fatty chain with a length of less than 16 carbon atoms, and mixtures thereof.

11. The composition of claim 1, wherein said vesicles of said second dispersion are formed of at least one lipid selected from the group consisting of:
sunflower lecithin;
soya lecithin/ethanol/water;
soya lecithin/cholesterol/propylene glycol; and
lauryl polyglyceryl-6-cetearyl glycol ether/dimyristyl phosphate.

12. The composition of claim 1, wherein said active agent of said first dispersion and said active agent of said second dispersion provide the same function and/or the same type of effect.

13. The composition of claim 1, wherein said active agent of said first dispersion and said active agent of said second dispersion are the same.

14. The composition of claim 1, further comprising:

(d) an oily phase dispersed in an aqueous phase.

15. The composition of claim 1, further comprising:

(d) a hydrophilic or lipophilic adjuvant.

16. A method for protecting, nourishing and/or firming the skin, comprising applying to the skin of a subject in need thereof an effective amount of a composition comprising a dispersion mixture of:

(a) a first dispersion of lipid vesicles which are capable of penetrating into the deep layers of the skin and which contain at least one active agent selected from the group consisting of protective, nutritive and firming agents, for treating these deep layers and (b) a second dispersion of lipid vesicles which are capable of penetrating into the layers of the stratum corneum of the skin and which contain at least one active agent selected from the group consisting of protective and nutritive agents, for treating these layers of the stratum corneum, and wherein said vesicles of said first dispersion ensure a distribution of N-(1-oxyl-2,2,6,6-tetramethyl-4-piperidyl)-N-dimethyl-N-hydroxyethylammonium iodide (ASL) in the stratum corneum $>1\times10^{-7}$ cm$^2$/s and in that said vesicles of said second dispersion ensure a distribution of ASL in the stratum corneum $<1\times10^{-7}$ cm$^2$/s.

17. A method of nourishing the skin, comprising applying to the skin of a subject in need thereof an effective amount of a composition comprising a dispersion mixture of:

(a) a first dispersion of lipid vesicles which are capable of penetrating into the deep layers of the skin and which contain at least one active agent selected from the group consisting of nutritive and firming agents, for treating these deep layers and (b) a second dispersion of lipid vesicles which are capable of penetrating into the layers of the stratum corneum of the skin and which contain at least one active agent selected from the group consisting of protective and nutritive agents, for treating these layers of the stratum corneum, and wherein said vesicles of said first dispersion ensure a distribution of N-(1-oxyl-2,2,6,6-tetramethyl-4-piperidyl)-N-dimethyl-N-hydroxyethylammonium iodide (ASL) in the stratum corneum $>1\times10^{-7}$ cm$^2$/s and in that said vesicles of said second dispersion ensure a distribution of ASL in the stratum corneum $<1\times10^{-7}$ cm$^2$/s.

* * * * *